United States Patent [19]

Yamato et al.

[11] Patent Number: 4,543,219
[45] Date of Patent: Sep. 24, 1985

[54] BAFFLE TRAY TOWER

[75] Inventors: Toshio Yamato, Takasaki; Tsutomu Ohba, Oita; Tunetoshi Kabata, Takasaki, all of Japan

[73] Assignee: Nippon Kayaku Kabushiki Kaisha, Tokyo, Japan

[21] Appl. No.: 550,196

[22] Filed: Nov. 9, 1983

[30] Foreign Application Priority Data

Nov. 24, 1982 [JP] Japan .................. 57-205627

[51] Int. Cl.⁴ ............................................. B01F 3/04
[52] U.S. Cl. ..................................... 261/109; 261/110
[58] Field of Search ......................... 261/109, 108, 110

[56] References Cited

U.S. PATENT DOCUMENTS

| | | | |
|---|---|---|---|
| 413,514 | 10/1889 | Jarrell | 261/109 |
| 732,548 | 6/1903 | Guillaume | 261/110 |
| 960,223 | 5/1910 | Guillaume | 261/110 |
| 1,557,112 | 10/1925 | Schneible | 261/108 |
| 1,562,760 | 11/1925 | Harris | 261/108 |
| 2,983,493 | 5/1961 | Handwerk | 261/109 |
| 3,218,046 | 11/1965 | Miers | 261/109 |
| 4,334,897 | 6/1982 | Brady et al. | 261/109 |
| 4,337,069 | 6/1982 | German, Jr. et al. | 261/110 |

FOREIGN PATENT DOCUMENTS

| | | | |
|---|---|---|---|
| 816692 | 10/1951 | Fed. Rep. of Germany | 261/108 |
| 1074199 | 3/1954 | France | 261/110 |

Primary Examiner—Tim Miles
Attorney, Agent, or Firm—Oblon, Fisher, Spivak, McClelland & Maier

[57] ABSTRACT

A baffle tray tower comprising a tubular tower body, a plurality stages of baffle tray members disposed within the tower body, and partition plates each disposed within the tower body so as to generally vertically divide a curtain zone defined between two adjacent stages of the baffle tray members into an upper curtain zone for mainly passing a gas therethrough and into a lower curtain zone for mainly passing a liquid therethrough can be operated as a gas-liquid contacting device with a high gas-liquid contact efficiency and a low pressure loss.

22 Claims, 12 Drawing Figures

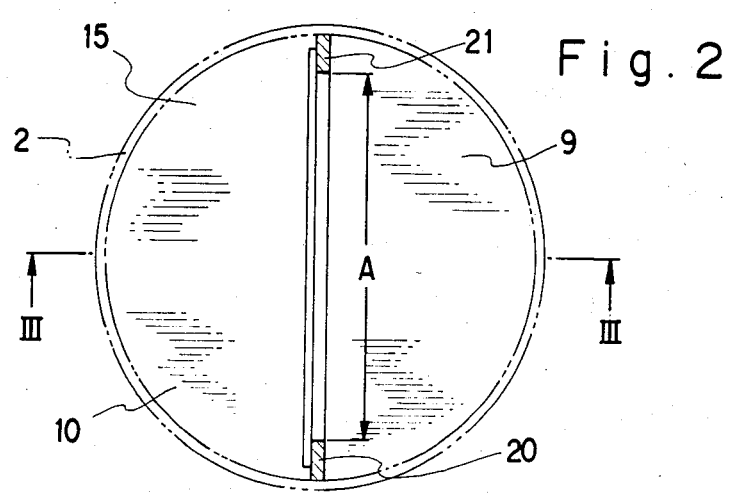

BAFFLE TRAY TOWER

This invention concerns a baffle tray tower and, more specifically, it relates to a baffle tray tower applied to the gas-liquid contacting operation such as gas absorption or distillation.

Packed towers or tray towers have heretofore been employed as the gas-liquid contacting device applied to the gas absorption, distillation or the like.

However, the packed tower has a drawback of giving a difficulty in scaling-up the tower since its operation efficiency is generally reduced as the diameter of the tower increases although the efficiency is good when the diameter of the tower is small, and in a necessity of determining the required packing height experimentally. In view of the above, the use of the packed tower with a large diameter is generally restricted only to the case where the number of theoretical plates is relatively small.

While on the other hand, the plate tower or column has a demerit of generally providing a great pressure loss although it can be used conveniently based on the established scaling-up technique. Furthermore, since the growth of polymer tends to occur on portions of the wall or the like in the tower to which the liquid does not contact sufficiently, the plate tower requires frequent maintainance when applied to the rectification of easily polymerizable unsaturated compounds.

Further, in view of the structure in the conventional baffle tray tower generally known so far, although the pressure loss can be reduced, effective contact between the gas and the liquid is difficult to be realized (low contact efficiency) since the gas stream passes through the curtain zone between the adjacent stages of the baffle trays while being spreaded over the entire zone. Therefore, the conventional baffle tray has scarcely been employed for the gas absorption or distillation, being used mainly for the heat transfer operation such as heating or cooling, dust collection and the like.

In the conventional baffle tray tower, the contact efficiency or the tray (plate) efficiency may be improved if the flow velocity of the gas is increased in the curtain zone, which can be attained by decreasing the interval between the baffle trays or reducing the tower diameter, but this would result in an increase in the flow velocity in the window zone leading to a greater pressure loss.

This invention has been accomplished in view of the foregoing problems and an object thereof is to provide a gas-liquid contacting baffle tray tower with a high gas-liquid contact efficiency and a low pressure loss.

According to this invention, the above-mentioned object can be attained by a baffle tray tower comprising a tubular tower body, a plurality stages of baffle tray means disposed within the tower body, and partition plates each disposed within the tower body so as to divide a curtain zone defined between two adjacent stages of the baffle tray means into an upper curtain zone for mainly passing a gas therethrough and into a lower curtain zone for mainly passing a liquid therethrough.

Another object of this invention is to provide a baffle tray capable of distillation or absorption operation reliably and over a long time for mixed liquid containing solid matters or easily polymerizable unsaturated compounds.

This object can be attained in accordance with a baffle tray tower having the foregoing constitution or, more preferably, with such a baffle tray tower in which each of the above-mentioned baffle tray means has an upper surface sloped such that the level of the tray means is lowered toward the side of the window.

This invention is to be described in more details referring to the accompanying drawings, by which the foregoing and other objects, as well as the features of this invention will be made clearer in which FIG. 1 is an illustrative perspective view for a baffle tray tower as a first embodiment of this invention;

FIG. 2 is an illustrative transversing cross sectional view for the baffle tray tower shown in FIG. 1;

FIG. 3 is an illustrative vertical cross sectional view taken along the line III—III in FIG. 2;

This invention will now be explained by way of a baffle tray tower 1 as the first preferred embodiment referring to FIG. 1 through FIG. 3.

Figure 1:
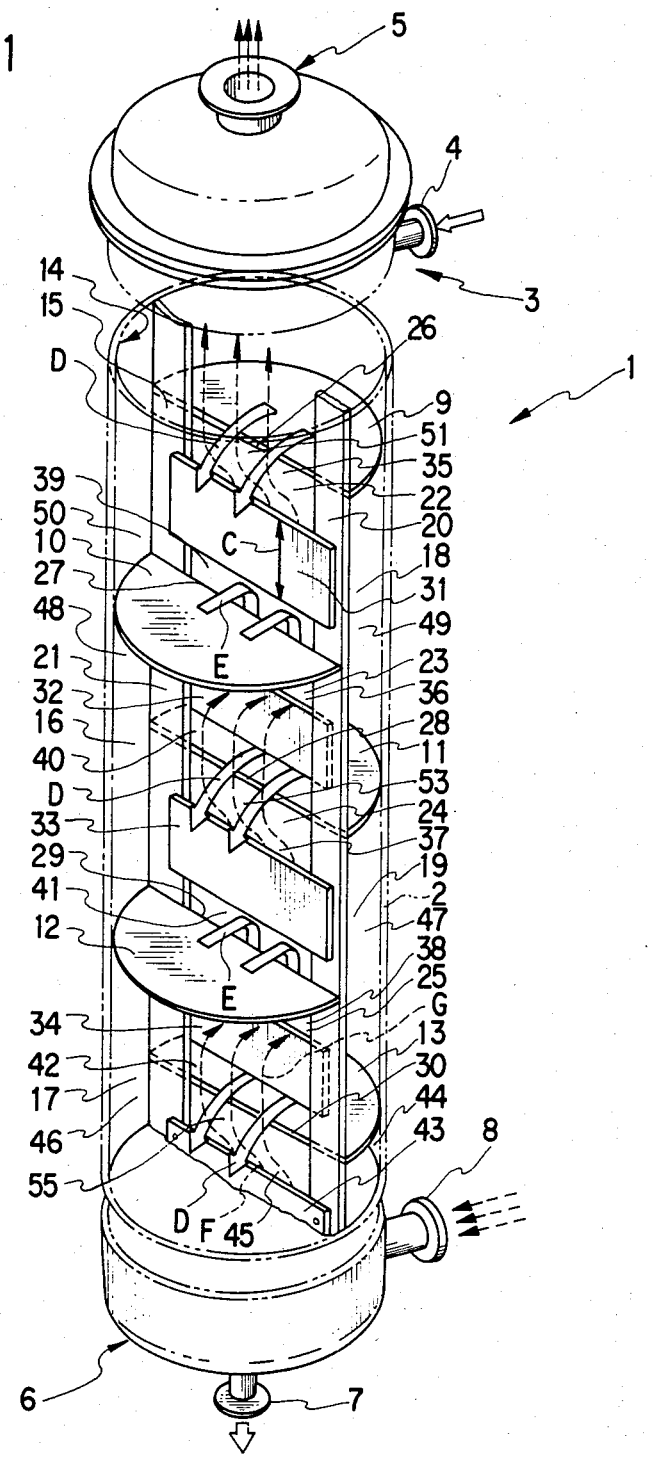

In FIG. 1 through FIG. 3, a cylindrical baffle tray body 2 is extended vertically and has a liquid inlet 4 and a gas exit 5 at its top 3, as well as a liquid exit 7 and a gas inlet 8 at its bottom 6.

Each of baffle trays 9, 10, 11, 12 and 13 as the baffle tray means is formed with a semi-circular plate which is in close contact at the arcuate edge thereof to the inner wall 14 of the tower body 2. The number of plates for the baffle trays is determined depending on the application use of the tower 1. Each of the baffle trays 9, 10, 11, 12 and 13 is disposed substantially horizontally and arranged at an equal interval in the vertical direction or the longitudinal direction of the tower body 2. Among the trays 9 to 13 illustrated in FIG. 1, the third tray 11 and the fifth tray 13 are situated just below the first tray 9, while the second tray 10 and the fourth tray 12 are situated just below a first window 15 of a semi-circular space area defined by the first tray 9 and the inner wall 14 of the tower main body 2. A third window 16 of a semi-circular space area complementary to the horizontal shape of the third tray 11 and a fifth window 17 of a semi-circular space area complementary to the horizontal shape of the fifth tray 13 are situated just below the first window 15, while a second window 18 of a semi-circular space area complementary to the horizontal shape of the second tray 10 and a fourth window 19 of a semi-circular space area complementary to the shape of the fourth tray 12 are situated just below the first tray 9.

The number of baffle trays is properly selected depending on the kinds of liquid and gas to be distilled or absorbed. The baffle trays at the odd number stages and the windows complementary in the shape to the baffle trays at the even number stages are of the substantially same shape and situated at the positions just aligned vertically to each other. In the same manner, the baffle trays at the even number stages and the windows complementary in the shape to the baffle trays at the odd number stages are of the substantially same shape and situated at the positions just aligned vertically to each other.

Curtain width control plates 20 and 21 are extended vertically along the inner wall 14 of the tower body 2 from the vicinity of the top 3 to the vicinity of the bottom 6 of the tower. The curtain width control plates 20 and 21 define the horizontal length, that is, the width A of curtain zones 22, 23, 24 and 25, the respective upper and lower edges thereof being defined with each pair of vertically adjacent trays 9, 10, trays 10, 11, trays 11, 12 and trays 12, 13, as well as support the baffle trays 9, 10, 11, 12 and 13 at their linear edges 26, 27, 28, 29 and 30, respectively.

Partition plates 31, 32, 33 and 34 divide the curtain zones 22, 23, 24 and 25 respectively into upper curtain zones 35, 36, 37 and 38 and into lower curtain zones 39, 40, 41 and 42, and the partition plates 31, 32, 33 and 34 transverse the vertical middle area of the curtain zones 22, 23, 24 and 25 and secured at both ends thereof to the curtain width control plates 20 and 21 respectively.

The partition plates 31 to 34 can eliminate the vertical middle zones in each of the curtain zones 22 to 25 where the contact efficiency has inevitably been lowered in the conventional baffle tray towers having no such partition plates 31 to 34.

The term curtain zones 22, 23, 24 and 25 used in this specification means those substantially or nearly vertical plane spaces, in which the upper and lower edges of each of them are defined with one of the baffle trays 9, 10, 11 and 12 and the respective one of the baffle trays 10, 11, 12 and 13 situated one stage below the abovementioned one of the baffle trays 9, 10 and 12 so as to receive a liquid flowing down from the linear edges 26, 27, 28 and 29 of one of the higher baffle trays 9, 10, 11 and 12. Both side edges of the curtain zones 22, 23, 24 and 25 are defined by the curtain width control plates 20 and 21 and the area of the curtain zone is defined as the maximum cross sectional area capable of passing therethrough the gas and the liquid to be contacted.

The lower curtain zones 39, 40, 41 and 42 are those areas which mainly pass the liquid. The area of each lower curtain zone, that is, the height B2 and the width A of the lower curtain zone is set to an appropriate size depending on the flow rate of the liquid to be contacted. For varying the curtain width A, the curtain width control plates 20 and 21 may be replaced with other plates of different width. Alternatively, each of the curtain width control plates 20 and 21 may, for example, be constituted with at least two plate members partially overlapped in the lateral direction with each other, and the relative position in the lateral direction of these two plate members for each control plate 21 or 22 may be changed by varying the laterally overlapping width for adjusting the curtain width. Moreover, it may be constructed to adjust the width for the upper curtain zone and the width for the lower curtain zone individually.

The upper curtain zones 35, 36, 37 and 38 are those areas which mainly pass a gas therethrough. The height B1 or the area [(width A)×(height B1)] for the upper curtain zone is set to an appropriate size depending on the flow rate of the gas to be contacted. Since a portion of the gas can pass through the lower curtain zones 39, 40, 41 and 42 as well, the height B2 or the area [(width A)×(height B2)] for the lower curtain zone may be also taken into the consideration in evaluating the flow rate of the gas, and the effective area for the curtain zone [(width A)×(height B1+B2)] is set to an appropriate size as a whole.

Assuming that the width for the curtain zone is substantially defined, the area for the upper and the lower curtain zones may be set appropriately by adjusting the position for the upper and lower edges of the partition plates 31, 32, 33 and 34, that is, the width i.e., height C and the position for the partition plates 31 to 34 depending on the flow rate of the gas. For changing the area of the upper and lower curtain zones, the vertical mounting positions of the partition plates or curtain area control plates 31, 32, 33 and 34 may be changed or the plates 31 to 34 may be replaced with other plates of different width C. Alternatively, each of the partition plates 31 to 34 may be constituted with at least two plate members partially overlapping in their width direction (vertical direction) and each of the width C for the partition plates 31 to 34 may be changed by changing relative position of the two plate members in the direction of their widths (by varying the overlapping width) to thereby change the area for at least one of the upper and lower curtain zones.

As described above, the baffle tray tower 1, having the partition plates 31 to 34, can be operated efficiently over a wide operating range, for example, from low to high production rate depending on the flow rate of the gas and liquid.

The curtain width control plates 20, 21 may not be provided if the partition plates 31, 32, 33 and 34 and the trays 9, 10, 11, 12, and 13 are secured directly to the tower body 2.

In the case of the buffle tray tower where a number of baffle trays are provided, the partition plates may not be provided in some of the curtain zones.

In the baffle tray tower 1, the flow velocity of the gas or vapor passing through the curtain zones is set usually at 2–10 m/sec in an atmospheric pressure system and at 3–20 m/sec in a reduced pressure system, but it is preferably set usually at 3–6 m/sec in the atmospheric pressure system and at 3–15 m/sec in the reduced pressure system, in order to keep the pressure loss low and the contact efficiency high.

In case of carrying out distillation under a reduced pressure in the baffle tray tower 1 comprising a number of trays for example, it is preferred to increase the height of the upper curtain zones 35, 36, etc. (that is, increasing the upper curtain area) toward the top of the tower and to decrease the height (that is, decreasing the upper curtain area) toward the bottom of the tower. The height for the lower curtain zones 39, 40, etc. may be different from each other as well. In this case, a highly efficient operation is possible depending on the change in the ratio of the flow rates of the gas and the liquid in the tower (from the top to the bottom of the tower).

A similar partition plate 43 may be disposed as well between the lowermost baffle tray 13 and the bottom 6 of the tower. In this case, the lower edge of the partition plate may be below the liquid level at the bottom of the tower.

The operation for the baffle tray tower 1 as the first embodiment according to this invention having the foregoing constitution will now be explained for a case where it is employed as an absorption tower.

A liquid introduced into the tower body 2 from the inlet 4 at the top 3 of the tower flows down onto the uppermost baffle tray 9 and the liquid on the tray 9 flows down from the edge 26 of the tray 9 through the window 15 onto the second tray 10 in the direction D in the form of a curtain-like thin film, thread or droplet stream. The liquid on the tray 10 flows down from the edge 27 of the tray 10 through the lower curtain zone 39 and the window 18 onto the third baffle tray 11 in the direction E in the form of the curtain-like thin film, thread or droplet stream. Then, the liquid flows down in the same manner through the lower curtain zones 40, 41, 42 and the adjacent windows 16, 19 and 17 onto the trays 12 and 13 in the direction D or E in the form of the curtain-like thin film, thread or droplet stream and, finally, flows down from the tray 13 to the bottom 6 of the tower and is then recovered from the exit 7.

Each tray may have a plurality of fine parallel grooves extended to the edge thereof on the upper surface of each tray so that the liquid may flow uniformly over the entire width of the tray edge.

While on the other hand, a gas introduced into the tower body 2 from the inlet 8 at the bottom 6 of the tower flows upwardly through the semi-circular post space 44 below the tray 13, enters into the semi-circular post space below the tray 12 passing through the curtain zone 45 in the direction F where it is in contact with the liquid stream in the direction D from the tray 13, passes through the window 17 while turning its direction upwardly along the inner wall 14 of the tower body 2, flows upwardly in the space 46 and, thereafter, passes from the space 46 through the upper curtain zone 38 in the direction G into the semi-circular post space 47 below the tray 11. The gas flowing in the direction G into the space 47 is in contact with the liquid flowing down in the direction E from the tray 12, passes upwardly in the space 47 through the window 19 while turning its direction upwardly along the inner wall 14 of the tower main body 2, passes from the space 47 through the upper curtain zone 37 in the direction F, contacts the liquid flowing down in the direction D from the tray 11 and then reaches the window 16. The gas having flown upwardly in the window 16 passes, in the same manner, through the semi-circular post space 48 below the tray 10, the upper curtain zone 36, the semi-circular post space 49 below the tray 9, the upper curtain zone 35 and the semi-circular post space 50 above the tray 10 successively and, finally, reaches the top 3 of the tower and is then sent out from the exit 5.

In the above process, gas-liquid contact is carried out between the liquid stream flowing down from the lower curtain zone situated just above each of the baffle trays in the direction D or E and the gas stream directly after passing through the upper curtain zone situated just below the baffle tray in the generally horizontal direction, that is, the direction F or G.

In the baffle tray 1, since the gas is selectively passed mainly through the upper curtain zones 35, 36, 37 and 38 by the presence of the partition plates 31, 32, 33 and 34, the gas stream can surely be brought into contact with the thin film-like liquid just after passing through the lower curtain zones, as compared with the conventional baffle tray tower without such partition plates when applied to gas-liquid contacting devices. Specifically, the liquid stream and the gas stream are brought into a close and concentrated contact at a comparatively high relative speed in restricted gas-liquid contact regions 51, 52, 53, 54 and 55, while the flow passage for the gas and the flow passage for the liquid are separated by the baffle trays and the partition plates in the semi-circular post spaces 46, 47, 48, 49 and 50 other than the contact regions 51 to 55. Consequently, since the gas stream can be rapidly separated from the liquid droplets after the contact in the course where the gas flows from a gas-liquid contact region to the suceeding gas-liquid contact region, a high gas-liquid contact efficiency can be obtained.

While on the other hand, in the baffle tray tower 1, since the gas flow velocity in the region other than the restricted region near the upper curtain zone is relatively low and the gas can flow slowly and smoothly through the semi-circular post space, the pressure loss in the gas can be kept lower.

The gas stream of a relatively high speed flux can be obtained by appropriately defining not only the height B1 but also the width A of the upper curtain zone. Specifically, the curtain width control plates 20 and 21 as well as the partition plates serve to gain the high speed flux of the gas stream passing through the region where the high speed flux of liquid is passed.

As described above, when the baffle tray tower 1 is applied as a reduced pressure distillation tower, because of its low pressure loss as well as high contact efficiency, the temperature at the bottom 6 of the tower can be lowered to thereby reduce the degradation of the liquid staying at the bottom 6, whereby heating by the steam at relatively low pressure and relatively low temperature can be employed in the course of distillation. On the other hand, in a case where the temperature at the bottom 6 of the tower is unchanged, since the temperature at the top 3 of the tower may be increased, inexpensive cooling water can be used for cooling distilled vapors instead of providing low temperature refrigerated water for the condenser at the top of the tower. Furthermore, since the contact efficiency is high and the pressure loss is low in this baffle tray tower 1, distillation in a single tower can be expected in such a case where it would otherwise be necessary to conduct the distillation by two towers in series due to the restriction in view of the temperature at the top and the bottom in the conventional tower.

In addition, since this baffle tray tower 1 produces less bubbles because of its structure, different from the conventional plate tower, it can be effectively applied even to easily bubbling liquid.

Furthermore, this baffle tray tower 1 is also suitable for the rectification of mixed liquid containing solid matters or easily polymerizable unsaturated compounds such as vinyl monomers.

The liquid in the form of the thin film or thread-like stream upon contact with the gas stream flowing along the direction G in the gas-liquid contact region, for example, the region 52, is scattered in the form of droplets 56, collides against the inner wall 14 of the tower body 2 and flows down along the inner wall 14 to the tray 11 while washing the inner wall 14. That is, since the inner wall 14 of the baffle tray tower 1 is always washed with the droplets containing a polymerization inhibitor, if unsaturated compound is condensed on the inner wall 14, the condensed droplets do not stay on the inner wall 14 for a long time, thereby enabling to avoid the polymer formation on a inner wall 14.

Furthermore, since the baffle tray is flat causing no substantial liquid hold-up on the surface thereof, the staying time of the liquid in the tower is relatively short to reduce the possibility of the polymer formation.

In addition, this baffle tray tower 1 has a simplified structure and can be fabricated with a reduced cost.

Figure 4:
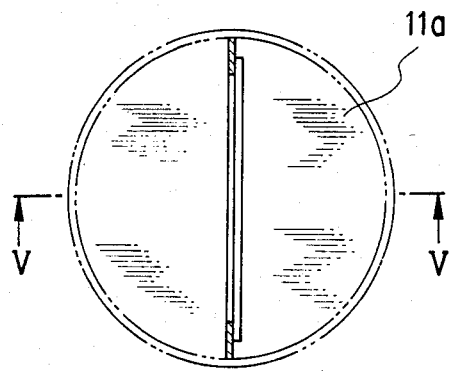
FIG. 4 is an illustrative transversing cross sectional view for the baffle tray tower as a second embodiment of this invention.
Figure 5:
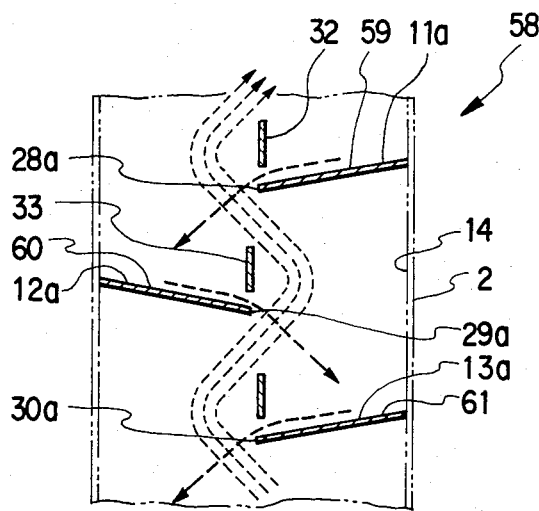
FIG. 5 is an illustrative cross sectional view taken along the line V—V in FIG. 4.

FIG. 4 and FIG. 5 show a portion of a baffle tray tower 58 as the second embodiment of this invention. In these figures, those components of a baffle tower 58 of the same function and configuration as those in the baffle tray tower 1 in the first embodiment carry the same or corresponding reference numerals.

In the baffle tray tower 58 of the second embodiment, each of the baffle trays 11a, 12a, 13a, etc. is disposed while slanted such that the height or level for the upper surfaces 59, 60, 61, etc. is lowered toward the curtain zone. Each of the trays 11a, 12a, 13a, etc. has a partially elliptic shape corresponding to the slope of the upper surface so that the linear edges 28a, 29a, 30a, etc. of the tray may be extended substantially horizontally in the diametrical direction of the tower body 2. The vertical cross sectional shape in FIG. 5 for each of the baffle trays 11a, 12a, 13a, etc. may be a wedged shape, instead of plate, so that the tray thickness is reduced toward the edges 28a, 29a, 30a, etc. In this case, the lower surface for each of the baffle trays 11a, 12a, 13a, etc. may be horizontal.

This baffle tray tower 58 can operate as a gas-liquid contacting device with a high contact efficiency and a low pressure loss in the same manner as the baffle tray tower 1 of the first embodiment. Furthermore, in this baffle tray tower 58, since the upper surfaces 59, 60, 61, etc. of the baffle trays 11a, 12a, 13a, etc. are lowered toward the edges 28a, 29a, 30a, etc., solid matters if contained in the liquid can be rapidly directed down along the slope to the bottom and discharged out of the tower 58. Accordingly, in the case where the baffle tray tower 58 is applied to the distillation of an easily polymerizable unsaturated compound, if the polymer seeds are included in the liquid of the unsaturated compound, the polymer seed or polymer can be rapidly flown down to the bottom along the slope of the trays 11a, 12a, 13a, etc. and discharged out of the tower body 2 before the polymer is formed or grown. As described above, this baffle tray tower 58, when applied to the distillation of the easily polymerizable unsaturated compound, can stably operate as a distillation tower over a long time with less fear of the polymer growth in the tower main body 2.

Furthermore, since there is little fear that the solid matters may remain or deposit in the tower main body 2, this baffle tray tower 58 is also suitable as a contacting device for liquid suspensions of polymer particles or sludges.

In addition to its low pressure loss, since the amount and the time of the liquid staying on the baffle tray are reduced in the baffle tray tower 58, it is suitable also to the distillation of temperature-sensitive materials, for example, those materials lacking in stability at high temperature.

Furthermore, since the liquid can be drained satisfactorily or substantially completely upon stopping of the tower operation and the stationary operation can be attained shortly after the start of the operation in this tower 58, the start and the stop for the operation can be facilitated.

In the baffle tray tower 58, the slopes for the baffle trays may be different at the upper and the lower portions of the tower 58, for example, the slope may be increased for the baffle trays nearer to the tower bottom.

The baffle tray means may comprise a plurality of baffle trays so that the contact efficiency per unit volume can be improved in the baffle tray tower.

Figure 6:
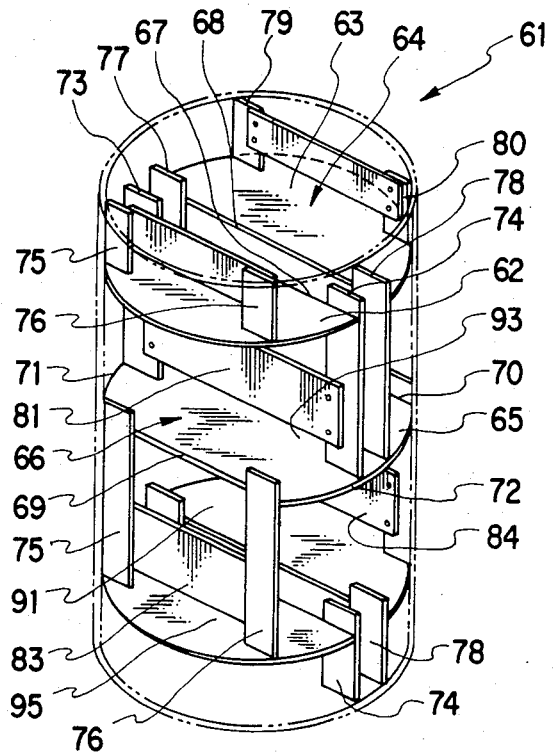
FIG. 6 is an illustrative perspective view for a baffle tray tower as a third embodiment of this invention.
Figure 7:
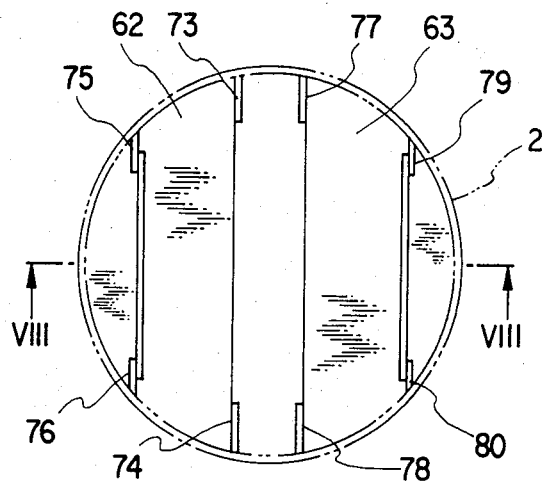
FIG. 7 is an illustrative transversing cross sectional view for the baffle tray tower shown in FIG. 6.
Figure 8:
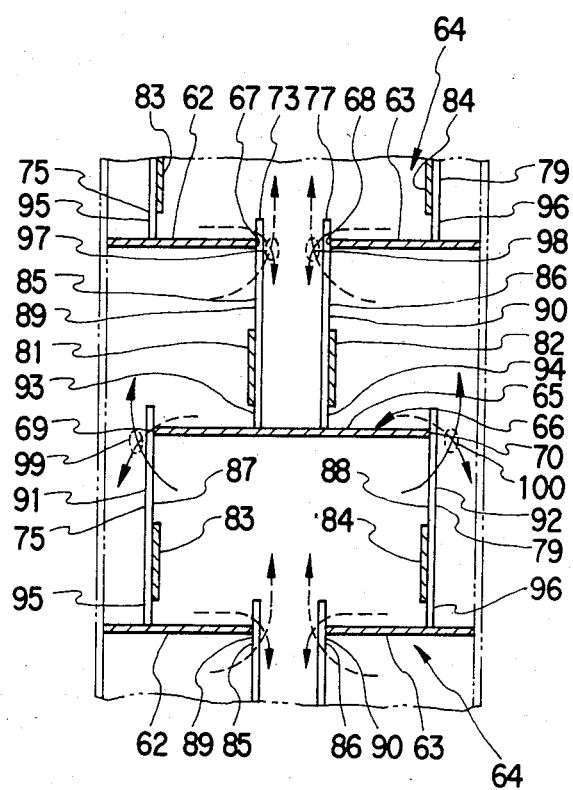
FIG. 8 is an illustrative vertical cross sectional view taken along the line VIII—VIII in FIG. 7.

FIG. 6 through FIG. 8 show a baffle tray tower 61 as the third preferred embodiment of this invention, in which a baffle tray means 64 comprising two baffle trays 62 and 63 of a same shape and a baffle tray means 66 comprising one baffle tray 65 are vertically disposed alternately.

The baffle trays 62 and 63 generally of a semi-circular plate shape are arranged substantially within a horizontal plane so that their linear edges 67 and 68 which are a little shorter than the diameter of the tower body 2 are opposed in parallel with each other. The other baffle tray 65 each having two parallel linear edges 69 and 70 of an identical length and two arcuate portions 71 and 72 in close contact with the inner wall of the tower main body 2 is disposed substantially horizontally between the upper and lower baffle trays means 64 so that the linear edges 69 and 70 are in parallel with the linear edges 67 and 68 of the baffle trays 62 and 63. The baffle trays 62 and 63 may be slanted such that the height or levels of the upper surface thereof are lowered toward the respective edges 67 and 68, and the baffle tray 65 may have an upper surface formed by connecting two planes slanted such that the height or level of the upper surface of the tray 65 is lowered toward both of the linear edges 69 and 70.

Curtain width control plates 73, 74, 75 and 76 are disposed between the baffle tray 62 and the baffle tray 65, while curtain width control plates 77, 78, 79 and 80 are disposed between the baffle tray 63 and the baffle tray 65. The curtain width control plates 73 to 80 connect the baffle trays 62, 63 and 65 securely. However, such curtain width control plates 73 to 80 may not be used in a case where the baffle trays 62, 63 and 65 are secured directly to the tower body 2.

Partition plates 81, 82, 83 and 84 are secured respectively at both ends thereof to the curtain width control plates 73 to 80 and the partition plates 81, 82, 83 and 84 divide the curtain zones 85, 86, 87 and 88 between the baffle tray means 64 and 66 into the upper curtain zones 89, 90, 91 and 92 and into the lower curtain zones 93, 94, 95 and 96 respectively.

In the baffle tray tower 61 of this third embodiment, two upper curtain zones and two lower curtain zones are formed between the baffle tray means 64 and the baffle tray means 66, by which the gas and liquid streams are brought into contact with each other in contact regions 97, 98, 99 and 100 and separated again after contact.

The width for the curtain width control plates 73, 74, 77 and 78 may be made greater than the width for the curtain width control plates 75, 76, 79 and 80, so that the widths for the curtain zones 85, 86, 87 and 88 may be identical. The tower body 2 may be made of a square tube or post member having an inner space in the form of a quadrangular prism and the width for the curtain zones 85, 86, 87 and 88 may be made of a same size.

Figure 9:
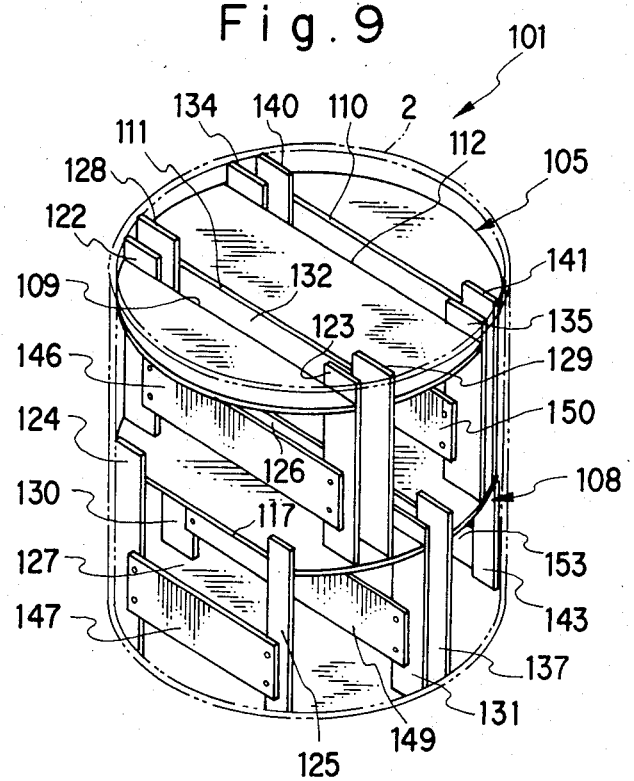
FIG. 9 is an illustrative perspective view for a baffle tray tower as a fourth embodiment of this invention.
Figure 10:
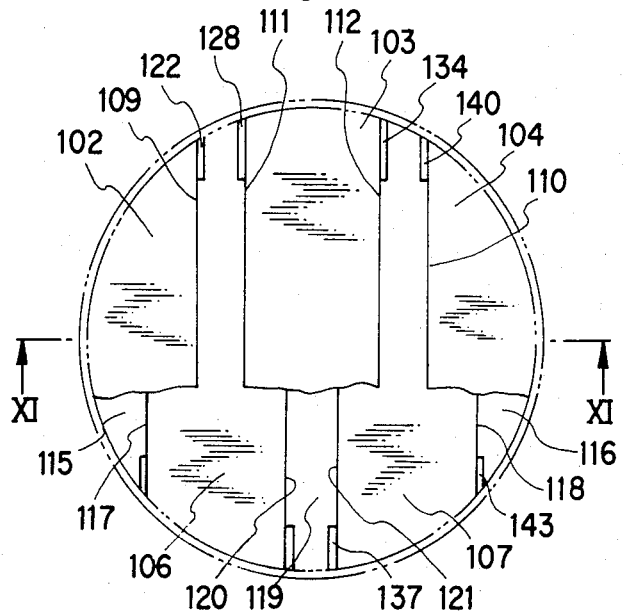
FIG. 10 is a partially broken illustrative transversing cross sectional view for the baffle tray tower shown in FIG. 9.
Figure 11:
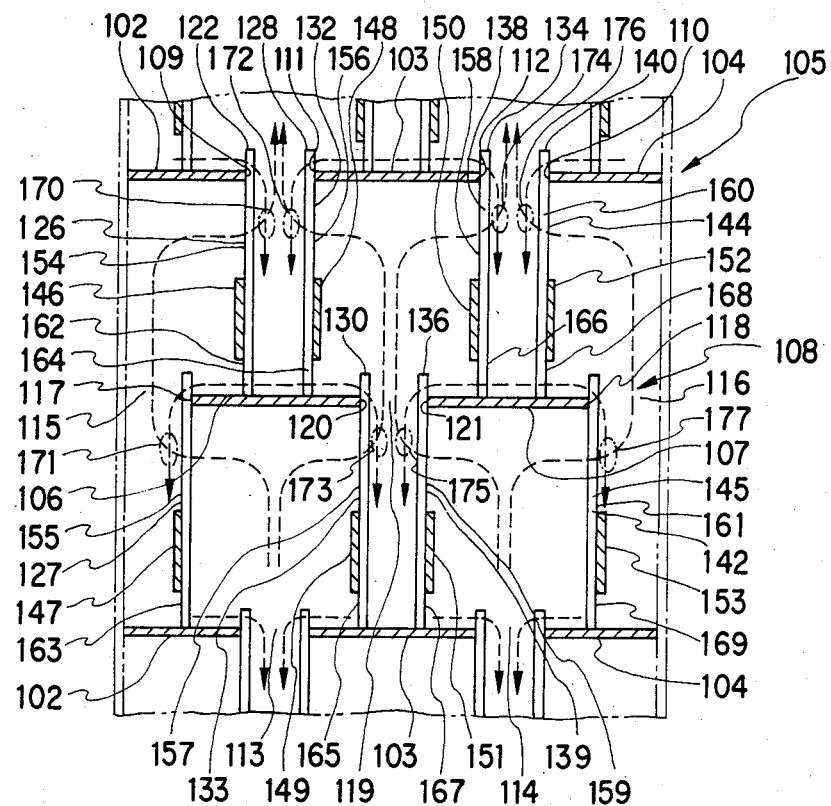
FIG. 11 is an illustrative vertical cross sectional view taken along the line XI—XI in FIG. 10.

FIG. 9 through FIG. 11 show a baffle tray tower 101 as the fourth embodiment of this invention. In the baffle tray tower 101, a baffle tray means 105 comprising three baffle trays 102, 103 and 104 and a baffle tray means 108 comprising two baffle trays 106 and 107 of a same shape are vertically disposed alternately.

The baffle trays 102 and 104 are of a same shape, and their linear edges 109 and 110 corresponding to chords of the circle are opposed in parallel with parallel linear edges 111 and 112 of the baffle tray 103 by way of gaps or windows 113 and 114 respectively.

The baffle trays 106 and 107 have linear edges 117 and 118 opposed to the inner wall 14 of the tower body 2 by way of gaps or windows 115 and 116 respectively and linear edges 120 and 121 in parallel with the linear edges 117 and 118 and opposed in parallel with each other by way of a gap or window 119 respectively. While the baffle trays 102, 103, 104, 106, 107 are disposed horizontally in the illustrated embodiment, each of the tray upper surface may be sloped or inclined such that the height or level of their upper surfaces are lowered toward the linear edges 109, 110, 111, 112, 117, 118, 120 and 121.

Curtain width control plates 122, 123, 124 and 125 are disposed between the baffle trays 102 and 106, in which the curtain width control plates 122 and 123 define the width for the curtain zone 126 and the width for the passage of a liquid flowing down from the edge 109, while the curtain width control plates 124 and 125 define the width for the curtain zone 127 and the width for the passage of the liquid flowing down from the edge 117. Curtain width control plates 128, 129, 130 and 131 are disposed between the baffle trays 103 and 106, in which the curtain width control plates 128 and 129 define the width for the curtain zone 132 and the width for the passage of the liquid flowing down from the edge 111, while the curtain width control plates 130 and 131 define the width for the curtain zone 133 and the width for the passage of the liquid flowing down from the edge 120.

Curtain width control plates 134 and 135, 136 and 137 are disposed between the baffle trays 103 and 107, in which the curtain width control plates 134 and 135 define the width for the curtain zone 138 and the width for the passage of the liquid flowing down from the edge 112, while the curtain width control plates 136 and 137 define the width for the curtain zone 139 and the width for the passage of the liquid flowing down from the edge 121.

Curtain width control plates 140, 141, 142 and 143 are disposed between the baffle trays 104 and 107, in which the curtain width control plates 140 and 141 define the width for the curtain zone 144 and the width for the passage of the liquid flowing down from the edge 110, while the curtain width control plates 142 and 143 define the width for the curtain zone 145 and the width for the passage of the liquid flowing down from the edge 118.

Partition plates 146, 147, 148, 149, 150, 151, 152 and 153 are supported at the respective both ends thereof to the corresponding paired curtain width control plates, and the partition plates 146 to 153 divide the curtain zones 126, 127, 132, 133, 138, 139, 144 and 145 respectively into upper curtain zones 154, 155, 156, 157, 158, 159, 160 and 161 and into the lower curtain zones 162, 163, 164, 165, 166, 167, 168 and 169.

In the baffle tray tower 101 of the fourth embodiment, four upper curtain zones and four lower curtain zones are formed between the baffle tray means 105 and the baffle tray means 108, by which the streams of the gas and liquid are brought into contact with each other in contact regions 170, 171, 172, 173, 174, 175, 176 and 177 and separated after contact.

The width and the height for the upper and the lower curtain zones can be controlled by adjusting the width for the curtain width control plates, as well as the width and position for the partition plates.

This baffle tray tower 101 of the fourth embodiment is suitable, for instance, as a tower of a large diameter. The tower body 2 may alternatively be made, for example, in the form of a square tube or post.

Figure 12:
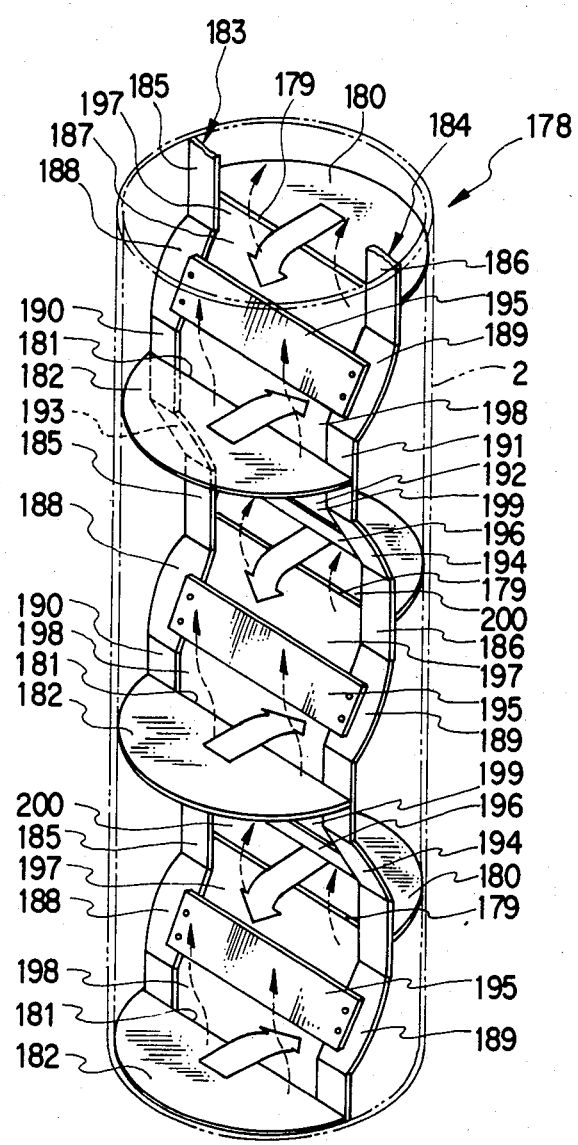
FIG. 12 is an illustrative perspective view for a baffle tray tower as a fifth embodiment of this invention.

FIG. 12 shows a baffle tray tower 178 as the fifth embodiment of this invention.

In the baffle tray tower 178, a baffle tray 180 of a semi-circular plate shape having a chord-like linear edge 179 which is a little smaller than the inner diameter for the tower body 2 and another baffle tray 182 of the same shape as the baffle tray 180 having a linear edge 181 in parallel with the linear edge 179 of the tray 180 are alternately disposed at an equal vertical distance along the longitudinal direction of the vertical tower body 2.

Curtain width control plates 183 and 184 comprise first vertical portions 185 and 186 extended vertically and supporting the baffle tray 180, first inclined portions 188 and 189 extended obliquely from the lower ends of the first vertical portions 185 and 186 along the curtain zone 187, second vertical portions 190 and 191 extended vertically from the lower ends of the first inclined portion 188 and 189 and supporting the baffle tray 182, and second inclined portion 193 and 194 extended obliquely from the lower ends of the second vertical portions 190 and 191 along the curtain zone 192 to the upper ends of the next first vertical portions 185 and 186.

A partition plate 195 is secured at both ends thereof to the inclined portions 188 and 189 and divides the curtain portion 187 into an upper curtain zone 197 and into a lower curtain zone 198. Another partition plate 196 is secured at both ends thereof to the inclined portion 193 and 194 and divides the curtain zone 192 into an upper curtain zone 199 and into a lower curtain zone 200.

In the baffle tray tower 178, a gas flowing upwardly through the upper curtain zone 197 is brought into contact with a liquid flowing down through the adjacent lower curtain zone 200 and then enters into the adjacent upper curtain zone 199 (a part of the gas also flows upwardly through the lower curtain zone 200). Then, the gas flowing upwardly through the upper curtain zone 199 is brought into contact with the liquid flowing down through the adjacent lower curtain zone 198 and then flowing upwardly to the adjacent upper curtain zone 197 (a portion of the gas also flows upwardly through the lower curtain zone 198).

In this baffle tray tower 178, since the area for the window is large, the pressure loss can be kept lower even if the diameter for the tower body 2 is small. The baffle tray may be sloped or inclined such that the upper surface of the baffle tray is lowered toward its edge or the window in front of the edge.

Although the baffle tray may be formed with a single plate, it can be formed with a plurality of plates joined to each other into a substantially integral single plate.

In the case of applying the baffle tray tower of this invention to absorption or distillation, the tray or plate efficiency reached as high as 15–25% and the pressure loss per one tray was as low as 5–15 mm aq.

This invention will now be explained by way of examples in which the absorption and distillation were carried out by using the baffle tray tower according to this invention.

EXAMPLE 1

The baffle tray tower 1 of the first embodiment shown in FIG. 1 through FIG. 3 was used as an absorption tower. In a vertical tower main body 2 with 7.8 cm of inner diameter, were disposed 5 stages of baffle trays 9, 10, 11, 12 and 13 horizontally with a 8.5 cm of vertical interval between the adjacent trays. The respective portions in the absorption tower 1 were sized as about 24 cm² area for each of the semi-circular windows 15, 18, 16, 19 and 17; 4.6 cm width A for each of the curtain zones 22, 23, 24 and 25; 4.6 cm width A and 2.1 cm height B1 for each of the upper curtain zones 35, 36, 37 and 38 (about 9.7 cm² area for each of the upper curtain zones); and 4.6 cm width A and 2.1 cm height B2 for each of the lower curtain zones 39, 40, 41 and 42 (about 9.7 cm² area for each of the lower curtain zones). To the absorption tower 1, were supplied nitrogen gas containing 1.5 mol% of acrolein vapors at a flow rate of 30 Nm³/hr 30 m³/hr at normal temperature of 0° C. and normal pressure of 760 mm Hg) from the inlet 8 and water at a flow rate of 40 l/hr from the inlet 4 to absorb acrolein into water. The tray efficiency of the baffle tray tower 1 was 18.6% and the pressure loss per one tray was 7.5 mm aq.

EXAMPLE 2

The baffle tray tower of the first embodiment shown in FIG. 1 through FIG. 3 was used as a distillation tower.

In a vertical tower body 2 with 75 cm of inner diameter, were disposed 10 stages of baffle trays 9, 10, etc. horizontally with a 63 cm of vertical interval between the adjacent trays. The respective portions in the distillation tower 1 were sized as about $2.2 \times 10^3$ cm² area for each of the semi-circular windows 15, 18, etc; 55 cm width A and 5 cm height B1 for each of the upper curtain zones 35, 36, etc. (about $2.8 \times 10^2$ cm² area); and 55 cm width A and 4 cm height B2 for each of the lower curtain zones 39, 40, etc. ($2.2 \times 10^2$ cm² area). To the distillation tower 1, were supplied a liquid containing 94.6% by weight of butylacrylate and 4.01% by weight of β-butoxybutylpropionate at a flow rate of 533 Kg/hr from the inlet 4 at the top 3 of the tower and steams, which had been obtained by heating the liquid from the exit 7 at the bottom 6 of the tower, through the inlet 8 and they were distillated. The distillation conditions were 105° C. and 340 mmHg at the top 3 of the tower and 158° C. and 341 mmHg at the bottom 6 of the tower. The vapor velocity in the upper curtain zone 35 in adjacent with the uppermost baffle tray 9 was 3.31 m/s. The tray efficiency was 21% and the pressure loss per one tray was as low as about 1.4 mm aq in this distillation tower.

EXAMPLE 3

The baffle tray tower 1 of the first embodiment shown in FIG. 1 through FIG. 3 was used as a distillation tower.

In a vertical tower body 2 with 170 cm of inner diameter, were disposed 80 stages of baffle trays 9, 10, etc. with a 30 cm of vertical interval between the adjacent trays. The respective portions in the distillation tower 1 were sized as $1.135 \times 10^4$ cm² area for each of the semi-circular windows 15, 18, etc.; $6.5 \times 10^2$ cm² area for each of the lower curtain zone 39, 40, etc.; and $1.989 \times 10^3$ cm² area for the uppermost upper curtain zone, which was gradually reduced down to $1.053 \times 10^3$ cm² area for the lowermost upper curtain zone, for each of the upper curtain zones 35, 36, etc. To the distillation tower 1, were supplied an acrylic acid solution containing 67.5 % by weight of acrylic acid, 1.9% by weight of acetic acid, 29.7 % by weight of isopropylacetate and 0.75% by weight of acrylic acid dimer at a flow rate of 3046 Kg/hr by way of an intermediate inlet onto the 51st baffle tray from the bottom and a portion of the distillate as a reflux at a flow rate of 3280 kg/hr from the inlet 4 at the top 3 of the tower. The distillation conditions were 36° C. and 80 mmHg at the top 3 of the tower and 93.5° C. and 147 mmHg at the bottom 6 of the tower. Distillates containing 5.67% by weight of acetic acid, 0.04% by weight of acrylic acid, and 94.1% by weight of isopropylacetate were obtained from the top 3 of the tower and concentrated acrylic acid containing 0.06% by weight of acetic acid and 2.7% by weight of acrylic acid dimer was obtained from the exit 7 at the bottom 6 of the tower. The pressure loss per one tray was as low as 11.4 mm aq. in the baffle tray tower.

The absorption tower or the distillation tower in the foregoing Examples 1-3 could be operated continuously for one year without observing the polymer formation at all in each of the towers.

As described above, in the baffle tray tower according to this invention, since the partition plates are disposed in the tower body for vertically dividing the curtain zones defined between the vertically adjacent baffle trays into the upper curtain zones mainly passing a gas therethrough and into the lower curtain zones mainly passing a liquid therethrough, the gas flowing upwards through the upper curtain zone and a liquid flowing downwards through the lower curtain zone just above and in adjacent with the upper curtain zone can be contacted effectively to each other and, as the result, the baffle tray tower can operate as a gas-liquid contacting device with a high contact efficiency and a low pressure loss.

Further, the baffle tray tower according to this invention can provide an excellent effect in that the inside of the tower is not contaminated at all with polymerized materials, when applied as the absorption or distillation tower for polymerizable unsaturated compounds, for example, vinyl monomers such as acrolein, acrylic acid, acrylic ester, methaclolein, methacrylic acid, methacrylic ester, acrylonitrile and methacrylonitrile.

Furthermore the baffle tray tower according to this invention is also applicable as the absorption or distillation tower for those liquids containing solid matters such as reaction products resulted from coal liquefation process.

What is claimed is:

1. A baffle tray tower for distillation or absorption of polymerizable unsaturated compounds comprising a tower body, a plurality of stages of baffle tray means disposed within said tower body, and partition plates, each disposed within said tower body transversing a vertically middle area of a curtain zone defined between two adjacent stages of said baffle tray means so as to divide the curtain zone into an upper curtain zone for mainly passing a gas therethrough and a lower curtain zone for mainly passing a liquid therethrough such that the upper curtain zone just below one baffle tray means allows the gas to be directed therethrough at increased speed to the liquid falling from said one baffle tray means.

2. The baffle tray tower of claim 1, in which said baffle tray means in each of the stages comprises a baffle tray and the edges of said baffle trays from which the liquid flows down are in parallel with each other.

3. The baffle tray tower of claim 2, in which the upper surface of the baffle tray is made horizontal.

4. The baffle tray tower of claim 2, in which curtain zone, the upper and the lower edges of which are defined by the edge of the baffle tray at the odd number stage and the edge of the adjacent baffle tray, is slanted with respect to the longitudinal direction of the tower body.

5. The baffle tray tower of claim 2, in which the baffle tray is sloped such that it is lowered toward the edge thereof from which the liquid flows down.

6. The baffle tray tower of claim 2, in which the baffle trays at each of the stages have a same shape, each of said baffle trays at the odd number stages is disposed at the position just aligning with other baffle trays at the odd number stages along the longitudinal direction at the tower body, and each of said baffle trays at the even number stages is disposed at a position just aligning with other baffle trays at the even number stages along the longitudinal direction of the tower body.

7. The baffle tray tower of claim 1, in which at least one of the baffle tray means at the odd number stage and the baffle tray means at the even number stage comprises a plurality of baffle trays.

8. The baffle tray tower of claim 7, in which the baffle tray means at one of the odd number stage and the even number stage comprises two baffle trays, said two baffle trays have edges opposing to each other so as to define a gap allowing the fluid to flow therethrough, the baffle tray means at the other of the odd number stage and the even number stage comprises one baffle tray, and said one baffle tray has two opposing edges so as to form two gaps between the inner wall of the tray body for allowing the fluid to flow therethrough.

9. The baffle tray tower of claim 7, in which the baffle tray means at one of the odd number stage and the even number stage comprises three baffle trays, said three baffle trays are disposed within the tray body so as to define two gaps for allowing the fluid to flow therethrough, the baffle tray means at the other of the odd number stage and the even number stage comprises two baffle trays, and said two baffle stages are disposed within the tray body so as to define three gaps for allowing the fluid to flow therethrough.

10. The baffle tray tower in any one of claims 2-5, 7-9, 1 or 6 in which a width for the curtain zone is made adjustable.

11. The baffle tray tower of claim 10, in which the width for the curtain zone is adjusted by a curtain width control plate disposed within the tower body.

12. The baffle tray tower in any one of claims 2-5, 7-9, 1 or 6 in which the position for the upper edge and/or lower edge of the partition plate in the longitudinal direction of the tower body is made adjustable so as to adjust the height for the upper and/or lower curtain zone.

13. The baffle tray tower of claim 12, in which position for the partition plate in the longitudinal direction of the tower main body is made adjustable.

14. The baffle tray tower in any one of claims 2-5, 7-9, 1 or 6, in which the tower body is of a cylindrical shape.

15. A baffle tray tower comprising:
(a) a baffle tray body extending vertically and having a top closure means and a bottom closure means, said top closure means having a liquid inlet and a gas exit therein and said bottom closure means having a gas inlet and a liquid exit therein, said baffle tray body having a central longitudinal plane extending along its axial length;
(b) a plurality of baffle trays mounted at spaced intervals in said baffle tray body, each of said plurality of baffle trays extending from the interior wall of said baffle tray body to said central longitudinal plane and having an inner edge surface located in said central longitudinal plane, alternate ones of said plurality of baffle trays extending from the interior wall of said baffle tray body in opposite directions; and
(c) a plurality of at least generally planar partition plates mounted in said baffle tray body, each of said at least generally planar partition plates:
  (i) having a central longitudinal plane which is coplanar with the central longitudinal plane of said baffle tray body;
  (ii) being spaced beneath a next higher adjacent one of said pluralty of baffle trays so that a planar upper curtain zone is defined in said central longitudinal plane between the lower, inner edge of said next higher adjacent one of said plurality of baffle trays and the upper edge of the generally planar partition plate; and
  (iii) being spaced above a next lower adjacent one of said plurality of baffle trays so that a planar lower curtain zone is defined in said central longitudinal plane between the upper, inner edge of said next lower adjacent one of said plurality of said baffle trays and the lower edge of the generally planar partition plate, whereby, in use:
(d) liquid enters said baffle tray body through the liquid inlet in said top closure means, flows downwardly from each one of said plurality of baffle trays to the next lower one of said plurality of baffle trays through one of said planar lower curtain zones, and exits said baffle tray body through the liquid exit in said bottom closure means;
(e) gas enters said baffle tray body through the gas inlet in said bottom closure means, flows upwardly from beneath each one of said plurality of baffle trays to beneath the next higher one of said plurality of baffle trays through one of said planar upper curtain zones, and exits said baffle tray body through the gas exit in said top closure means; and
(f) the liquid and the gas flow through each other in counter-current fashion as the liquid flows downwardly from each one of said plurality of baffle trays to the next lower one of said plurality of baffle trays.

16. A baffle tray tower as recited in claim 15 wherein:
(a) said baffle tray body is cylindrical in shape;
(b) said baffle trays are at least generally semi-circular in shape; and
(c) said partition plates are at least generally rectangular in cross-section perpendicular to said central longitudinal plane.

17. A baffle tray tower as recited in claim 15 wherein the upper surfaces of said plurality of baffle trays are at least generally horizontal.

18. A baffle tray tower as recited in claim 15 wherein the upper surfaces of said plurality of baffle trays are inclined downwardly towards their inner edges.

19. A baffle tray tower comprising:
(a) a baffle tray body extending vertically and having a top closure means and a bottom closure means, said top closure means having a liquid inlet and a gas exit therein and said bottom closure means having a gas inlet and a liquid exit therein, said baffle tray body having a central longitudinal plane extending along its axial length;
(b) a plurality of baffle trays mounted at spaced intervals in said baffle tray body, each of said plurality of baffle trays extending from the interior wall of said baffle tray body to an inner edge surface located adjacent to, but short of, said central longitudinal plane, alternate ones of said plurality of baffle trays extending from the interior wall of said baffle tray body in opposite directions; and
(c) a plurality of at least generally planar partition plates mounted in said baffle tray body, each of said at least generally planar partition plates:
  (i) having an upper edge, a lower edge, and a central transverse axis which is located in said central longitudinal plane;
  (ii) being spaced beneath a next higher adjacent one of said plurality of baffle trays so that a planar upper curtain zone is defined between the lower, inner edge of said next higher adjacent one of said plurality of baffle trays and the upper edge of the generally planar partition plate;
  (iii) being spaced above a next lower adjacent one of said plurality of said baffle trays so that a planar lower curtain zone is defined between the upper, inner edge of said next lower adjacent one of said plurality of baffle trays and the lower edge of the generally planar partition plate; and
  (iv) being disposed so that it cuts said central longitudinal plane, its upper edge being on the side of said central longitudinal plane adjacent said next higher adjacent one of said plurality of baffle trays and its lower edge being on the side of said central longitudinal plane adjacent said next lower one of said plurality of baffle trays, whereby, in use:
(d) liquid enters said baffle tray body through the liquid inlet in said top closure means, flows downwardly from each one of said plurality of baffle trays to the next lower one of said plurality of baffle trays through one of said planar lower curtain zones, and exits said baffle tray body through the liquid exit in said bottom closure means;
(e) gas enters said baffle tray body through the gas inlet in said bottom closure means, flows upwardly from beneath each one of said plurality of baffle trays to beneath the next higher one of said plurality of baffle trays through one of said planar upper curtain zones, and exits said baffle tray body through the gas exit in said top closure means; and
(f) the liquid and the gas flow through each other in counter-current fashion as the liquid flows downwardly from each one of said plurality of baffle trays to the next lower one of said plurality of baffle trays.

20. A baffle tray tower as recited in claim 19 wherein:
(a) said baffle tray body is cylindrical in shape;
(b) said baffle trays are at least generally semi-circular in shape; and
(c) said partition plates are at least generally rectangular in cross-section perpendicular to said central longitudinal plane.

21. A baffle tray tower as recited in claim 19 wherein the upper surfaces of said plurality of baffle trays are at least generally horizontal.

22. A baffle tray tower as recited in claim 19 wherein the upper surfaces of said plurality of baffle trays are inclined downwardly towards their inner edges.

* * * * *